(12) United States Patent
Riess

(10) Patent No.: US 6,241,655 B1
(45) Date of Patent: Jun. 5, 2001

(54) DEVICE FOR LOCALLY IMMOBILIZING A BEATING HEART

(76) Inventor: Andreas G. Riess, Langer Kamp 72, D-22850 Norderstedt (DE)

( * ) Notice: Subject to any disclaimer, the term of this patent is extended or adjusted under 35 U.S.C. 154(b) by 0 days.

(21) Appl. No.: 09/418,740

(22) Filed: Oct. 15, 1999

Related U.S. Application Data

(63) Continuation of application No. PCT/EP98/02235, filed on Apr. 16, 1998.

(30) Foreign Application Priority Data

Apr. 29, 1997 (DE) .......................................... 297 07 567 U

(51) Int. Cl.[7] .................................................. A61M 35/00
(52) U.S. Cl. .............................................................. 600/37
(58) Field of Search ................................ 600/36, 37, 16, 600/201, 210, 213, 235; 606/232–234, 7, 15, 139, 191

(56) References Cited

U.S. PATENT DOCUMENTS

| 4,159,720 | * | 7/1979 | Burton ................................. 606/232 |
| 5,782,746 | * | 7/1998 | Wright ................................... 600/37 |
| 5,885,271 | * | 3/1999 | Hamilton et al. ..................... 600/201 |
| 5,976,069 | * | 11/1999 | Navia et al. ............................ 600/37 |
| 6,010,525 | * | 1/2000 | Bonutti et al. ....................... 606/232 |
| 6,033,362 | * | 3/2000 | Cohn .................................... 600/213 |

FOREIGN PATENT DOCUMENTS

| 0 820 721 | 1/1998 | (EP) . |
| 95 17127 | 6/1995 | (WO) . |
| 97 10753 | 3/1997 | (WO) . |
| 98 48704 | 11/1998 | (WO) . |

\* cited by examiner

*Primary Examiner*—John P. Lacyk
*Assistant Examiner*—Joseph A. Cadugan
(74) *Attorney, Agent, or Firm*—Barry R. Lipsitz

(57) ABSTRACT

A device is provided for locally immobilizing a beating heart, in order to avoid tears or hematomas of the heart tissue during the application of strong pressure or suction forces. The device is particularly useful during an anastomosis procedure between a bypass conduit and a coronary vessel of the anterior wall of the left ventricle. The device includes a fork-like platform with two essentially parallel fork blades that form an intermediate space therebetween. The intermediate space has a width which corresponds to one to five times the width of a coronary vessel that is to be arranged in the intermediate space. At least one opening is provided on each of the fork blades adjacent to the intermediate space. Elements that can be guided through the openings and secured to a fixing device are provided for winding around the coronary vessel.

27 Claims, 11 Drawing Sheets

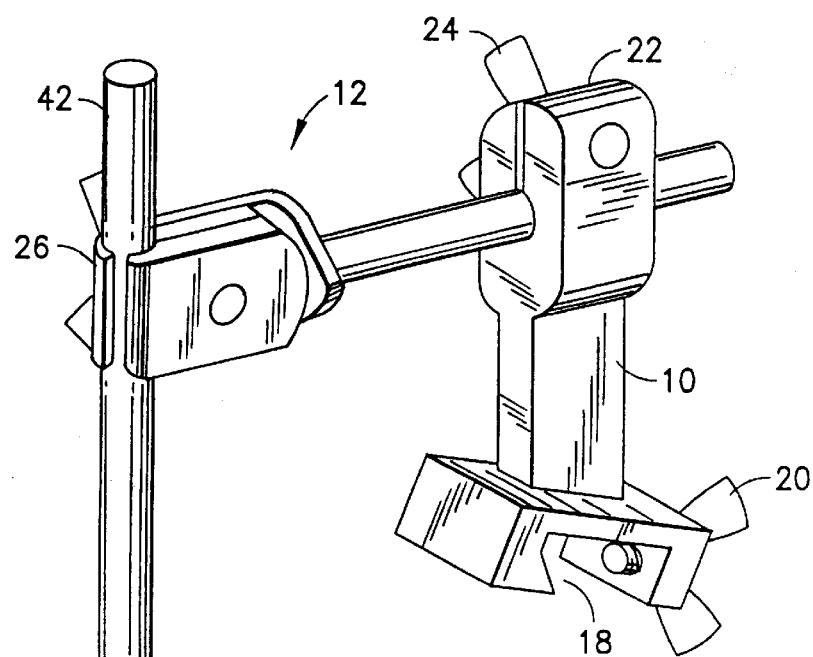
FIG.5
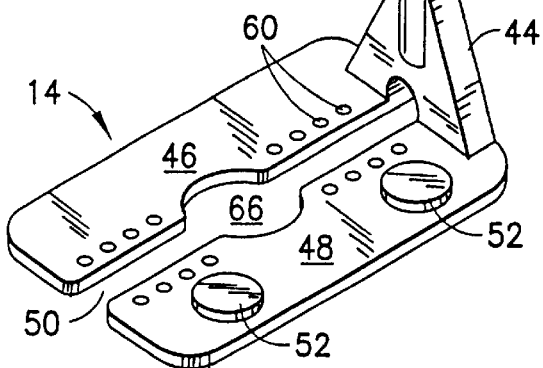

DEVICE FOR LOCALLY IMMOBILIZING A BEATING HEART

This application is a continuation of international application number PCT/EP 98/02235, filed Apr. 16, 1998.

BACKGROUND OF THE INVENTION

The invention relates to a device for locally immobilizing a beating heart, in particular, for the purpose of carrying out anastomosis between a bypass conduit and a coronary vessel of the anterior wall of the left ventricle of the heart, comprising a fork-shaped platform with two fork blades which extend essentially parallel and form an intermediate space between them.

Minimally invasive operating techniques are the trend and experience keen interest, particularly today with the background of the necessity for saving on costs. In this respect, it is not, however, exclusively the costs which are of concern. The reduction in the preoperative, intraoperative and postoperative trauma, the shortened operating and anesthetic times, the quicker healing of wounds, shorter in-patient times and less wound pain as well as the cosmetic result are also important arguments for minimally invasive operating techniques. In all fields of surgery attempts are being made to replace the standard procedures by minimally invasive variations. For example, reference is merely made to the video-controlled trephine technique for gynecological procedures.

Cardiosurgery procedures with their low mortality and morbidity in relation to the size of the operation first became possible during the 1950s as a result of the development of the heart-lung machine. This allows operations to be carried out on an immobilized and bloodless heart for a period of time of several hours. For several decades operations on hearts with a heart-lung machine were the golden standard.

In a substantial development, specific coronary operations were later carried out on a beating heart with minimally invasive operating techniques, wherein the use of the heart-lung machine became superfluous. The motivation for this course of action was the increasing knowledge about the side effects and disadvantages of the cardiopulmonary bypass (CPB). The contact of the blood with plastic surfaces of the heart-lung machine leads to an activation of the so-called coagulation cascade and the complement system. To prevent any formation of blood clots in the heart-lung machine as a result of this and therefore to a blockage thereof, high doses of heparin are required. As a result of the complete elimination of blood-clotting effected as a result, complications with bleeding may occur during and after procedures using heart-lung machines. As a result, the administration of foreign blood with all its possible consequences (hepatitis, HIV, inter alia) may become necessary. The blood platelets which are essential for normal blood clotting are also, in some cases, impaired considerably in their number and also in their functioning due to a procedure with a heart-lung machine and this again entails the risk of an increase in bleeding complications.

It is not, therefore, surprising that one result of randomized prospective studies with larger numbers of patients was that the patients who had operations on a beating heart without a heart-lung machine had, postoperatively, a statistically significantly lower loss of blood than the patients who were operated on with a heart-lung machine. The fact that the entire sternum normally has to be opened up during procedures with a heart-lung machine can lead to postoperative pain in the wound area but also to disorders during the healing of wounds and instabilities of the sternum. Additional side effects of procedures with a heart-lung machine are neurological complications which are attributed to the extracorporeal circulation. For example, small micro-clots but also air embolisms may reach brain arteries where they trigger strokes. An additional source of thromboembolic complications may be fine arteriosarcleroses in the area of the aorta which may be divulsed as a result of the manipulations carried out thereon (connection to the heart-lung machine and clamping off or lateral clamping out of the aorta). Moreover, it is known for not just a few patients to have neurological failures to a slight degree or psychiatric peculiarities (up to 30 percent) following a procedure with a heart-lung machine and cardioplegic ventricular standstill.

In comparison with this, the minimally invasive supply of the most important vessel of the left-ventricular anterior wall (LAD artery) without a heart-lung machine offers numerous advantages. The operation may be performed more quickly by an experienced surgeon than a procedure with a heart-lung machine. The patients have a smaller scar and thus a cosmetically better result is achieved. The sternum retains some of its stability since it is opened up only partially. This causes less wound pain and makes a generally uncomplicated healing phase of the bone possible. In the case of the LIMA/LAD (sternum artery/coronary vessel) procedure, the most important vessel of the heart (LAD) is supplied with the best bypass conduit (LIMA). Up to 80 percent of the entire blood requirements of the heart may be covered by the LAD artery. After a single LIMA onto the LAD, even when additional stenoses exist in smaller branches, most of the patients have no troubles after a successful operation even when the other stenoses remain untreated. Nevertheless, these stenoses, insofar as they are present, should be dilated after a successful minimally invasive LIMA/LAD procedure with a then lesser risk from a prognostic point of view since the LAD has been taken care of beforehand. If the patency rate of the various bypass types onto the various heart vessels is observed, what has been said above becomes even clearer. The sternum artery supply of the LAD has a 10 year patency rate of over 93 percent. In contrast to this, the vein bypasses can already display changes in the vessel inner walls after a few years, and the patency rate of vein bypasses, depending on the vessel to which they have been sutured, is only between 40 and 80 percent for 10 years.

Additional advantages with minimally invasive surgery are the short anesthetic times, extubation generally taking place on the operating table, a stay in the intensive care unit of only a few hours and an overall stay in hospital of approximately two to four days. This is advantageous for the patient and costs can be reduced. Furthermore, as a result of the smaller wound area fewer adhesions occur between pericardium and heart which can be of importance for any later re-operations. Moreover, it is reported in studies that the occurrence of cardiac dysrhythmia during the postoperative period of time following minimally invasive heart surgery procedures is less.

To carry out the anastomosis between LIMA and LAD, the anastomosis area must be immobilized at the beating heart in order to be able to carry out the approximately 15 stitches in an area of a few millimeters with the required precision.

The LIMA/LAD procedure on the beating heart is known and is practiced. In this respect, a so-called mini-sternotomy is carried out on the ventilated patient. A skin incision of approximately eight centimeters in length is made beginning at approximately two centimeters above the metasternum as far as the level of the fourth intercostal space (ICR).

Subsequently, a partial median sternotomy is carried out as far as the left third ICR. The LIMA is prepared under direct view of the eye as far as approximately the second ICR. Subsequently, the clotting time of the blood is protracted by administering 5000 to 7500 units of heparin intravenously. Subsequently, the LAD is looped around and thereby occluded distally and proximally of the area selected for the anastomosis. During the end-to-side anastomosis between LIMA and LAD carried out subsequently with a continuous 8-0 suture, it is of greatest significance for the quality of the anastomosis and thus for the success of the operation as a whole how successfully the anastomosis area is stabilized.

Various tools have been developed for this and some of these have to be held by an assistant or secured in various ways. These tools either have to be pressed onto the operating area under high pressure or have suction pads, with the aid of which the heart is lifted. In both cases, it is, however, particularly disadvantageous that tears or hematomas can occur in the heart tissue due to the strong compression or suction forces.

The object of the present invention is to make an improved device of the above-mentioned type available which eliminates the above-mentioned disadvantages.

SUMMARY OF THE INVENTION

This object is accomplished by a device of the above-mentioned type having the features characterized in claim 1.

For this purpose, it is inventively provided in a device of the above-mentioned type for the intermediate space to have a width which corresponds to 1 to 5 times the width of a coronary vessel to be arranged in the intermediate space, wherein at least one opening is provided adjacent to the intermediate space on each of the fork blades, wherein, in addition, means are provided for winding around the coronary vessel which can be guided through the at least two openings and can be secured to at least one fixing device provided on the fork blades. The idea is thereby essentially to dispense completely with the depression for the purpose of stabilization. On the contrary, the platform is lowered onto the LAD and thus restrained in the area of the circle-like enlargement for the purpose of fixing it. The concept aims at keeping friction as small as possible and thereby hindering the heart as little as possible in its movement. In this respect, the surface area of the fork blades is comparatively large and on the underside flat and smooth. The central point is that the immobilization of the LAD is accomplished simply by way of its restraining, and thus the drawing of the anastomosis area into the circle-like enlargement of the platform gap. Frictional forces are not required for this type of fixing in position.

This has the advantage that with an improved stabilization and optimum accessibility of the coronary vessel to be operated for the surgeon, the traumatism of the heart tissue is minimized at the same time.

Additional advantages of the inventive device are as follows:

A mini-sternotomy with a length of, for example, 8 to 10 cm is made possible. This avoids the asymmetric opening with separation of the musculature as well as of the vessel/nerve bundle of the ICR. As a result, the wound pains of a lateral thoracotomary, which are sometimes considerable and often require the administration of opiates over a longer period of time, are avoided. In contrast thereto, surprisingly little postoperative pain occurs with the median sternotomy and, in particular, with the mini-sternotomy and so the postoperative need for analgesics is low.

A maximum immobilization of the anastomosis area takes place with a simultaneously optimum adjustability, minimum impairment of the heart functioning by the device and minimum traumatism of the heart as a result of the contact with the inventive device. The surgeon has a free view of the operating area and the heart movement is visually shielded. It has been shown in operating practice that the action of the beating heart represents a visual impairment of the operating area which makes concentration on the comparatively small anastomosis area more difficult.

The possibility of fixing the LAD to the fork plates with corresponding means results in a considerably higher safety during use and an improved immobilization of the operating area without the necessity for bearing pressure on the heart muscles.

The device can be mounted quickly and easily and demounted in seconds. If, during the occlusion of the LAD, stronger hemodynamic impairments of the pumping function of the heart or malign cardiac dysrhythmia occur, it may be necessary to change the operating strategy and complete the median sternotomy and continue the operation with the aid of the heart-lung machine. In order to keep the period of time of a hemodynamic impairment and thus the phase of a situation of oxygen deprivation of the brain as short as possible it is necessary for an inserted stabilization platform to be demountable in seconds.

As a result of the comparatively small contact surface of previous solutions, kinking of the heart muscle occurs to a greater or lesser extent and thus traumatism thereof during the pressure on the heart muscle at the circumferential edges. In accordance with the invention, the surface area of the fork blades is dimensioned to be of such a size that no kinking of the heart muscle at the circumferential edges can occur. On the contrary, the LAD artery with its accessory tissue is held by the edge of the fork blades only in the area of the gap. The combined surface area of the two platform blades is, for example, 7 to 30 square centimeters, in a preferred embodiment 15 square centimeters.

At least one circle-like enlargement of the intermediate space is expediently provided. This allows the surgeon improved access to the coronary vessel fixed in the device. The circle-like enlargement preferably has a diameter of 8 mm to 12 mm, in particular of 10 mm.

In a particularly advantageous manner, the fixing means is at least one shaped stud with a mushroom-like cross section. This allows a simple and rapid securing of the means for winding around the coronary vessel on the inventive device.

As a result of the fact that the at least two openings are each formed on one fork blade, a vessel to be operated on may be clamped in the intermediate space with the means for winding around the vessel and thus be effectively stabilized or rather immobilized.

Expediently, the at least two openings are bores in the fork blades.

A threading and unthreading of the means for winding around the coronary vessel through the openings in the fork blades is avoided by providing slots in the fork blades which each extend from the intermediate space to one opening. Expediently, the slots are each designed in a hook or S shape so that any unintentional slipping of the means for winding around the coronary vessel out of the openings is prevented.

A particularly gentle and secure abutment of the device on the heart is achieved in that at least one fork blade is chamfered towards the intermediate space on a side abutting on the heart. The angle of chamfer is preferably 5 to 15 degrees, in particular 10 degrees.

Expediently, the intermediate space has a width of 4 mm to 10 mm, in particular of 6.5 mm. As a result, the intermediate space offers in a particularly advantageous manner only room for one tissue fold and thus a coronary vessel can be fixed so as to be exactly positioned in the intermediate space without any great lengths for the means for winding around the coronary vessel needing to be clamped.

Expediently, the means for winding around the coronary vessel is at least one thread or at least one vessel loop (hollow rubber bridle).

In a particularly preferred further development of the invention, the intermediate space has a width which corresponds to 1 to 2 times, 1 to 3 times or 2 to 3 times the width of the coronary vessel to be arranged in the intermediate space.

Expediently, the intermediate space has such a width that a coronary vessel may be arranged in it in such a manner that this has lateral distances to the fork blades which are each equal to or smaller than the width of the coronary vessel.

The device may be attached to the surface of the heart in a particularly good manner in that the fork blades are connected to one another via a bridge which has an essentially semicircular recess between two arms, on each of which one fork blade is arranged. This recess preferably has a radius of 2 mm to 5 mm (half the width of the gap), in particular of 3.25 mm.

BRIEF DESCRIPTION OF THE DRAWINGS

The invention will be explained in greater detail in the following on the basis of the attached drawings. These show in FIG. 1 an inventive device in a perspective view, FIG. 2 in a front view, FIG. 3 in a plan view, FIG. 4 a fixing device in a sectional view, FIG. 5 an inventive device with fixing means in a perspective view, FIG. 6 in a further perspective view, FIG. 7 a crossbar joint in an exploded illustration, FIG. 8 an arrangement mounted during an operation in a perspective view, FIGS. 9 and 10 an illustration of the fixing of a coronary vessel on an inventive device in a perspective view, FIG. 11 an enlarged illustration of a vessel fixed in the inventive device, FIGS. 12A to 12D a sectional view of various conditions of the heart with a coronary vessel fixed in the inventive device, FIG. 13 a second embodiment of an inventive device, FIG. 14 a third embodiment of an inventive device and FIGS. 15 and 16 preferred embodiments of fork surfaces.

The inventive device illustrated in FIGS. 1 to 3 and 5 to 8 comprises essentially three parts: An upright 10, a crossbar 12 and a platform 14. The upright 10 slides with a connection member 16, for example, on the base of a BIRNBAUM retractor 16 and may be fixed in any reachable position as a result of tightening a wing bolt 20. It bears the crossbar 12 at an angle of 90 degrees in a joint 22 which allows the crossbar 12 to slide back and forth as well as be turned about its longitudinal axis through any optional angle (cf.

Figure 7:
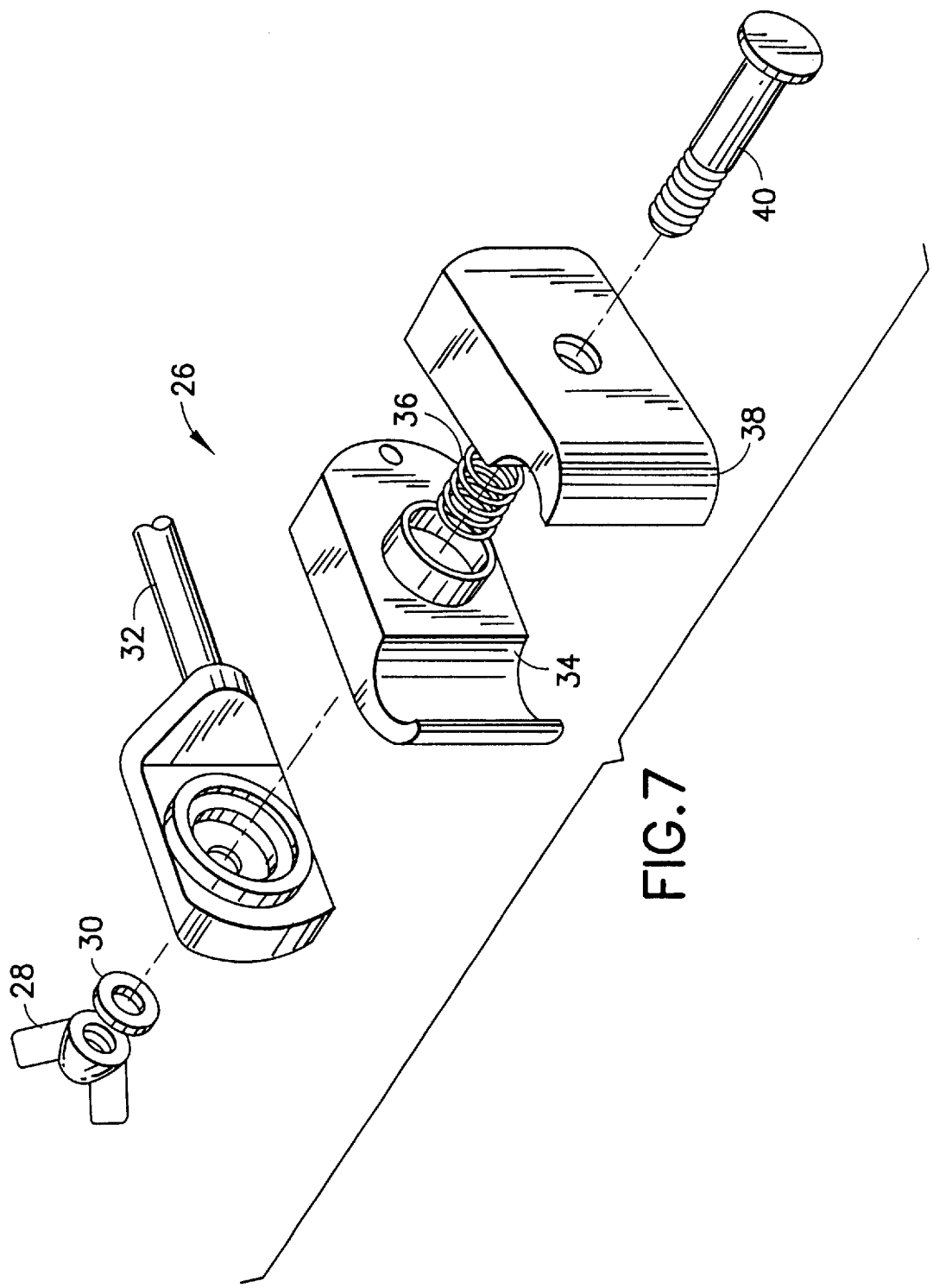

An additional joint 26 is arranged on the crossbar 12 at one end. This is illustrated in detail in FIG. 7 and comprises a wing nut 28, a washer 30, a crossbar shaft 32, an inner shell 34, a pressure spring 36, an outer shell 38 and a screw bolt 40, for example, an M6 bolt.

Figure 6:
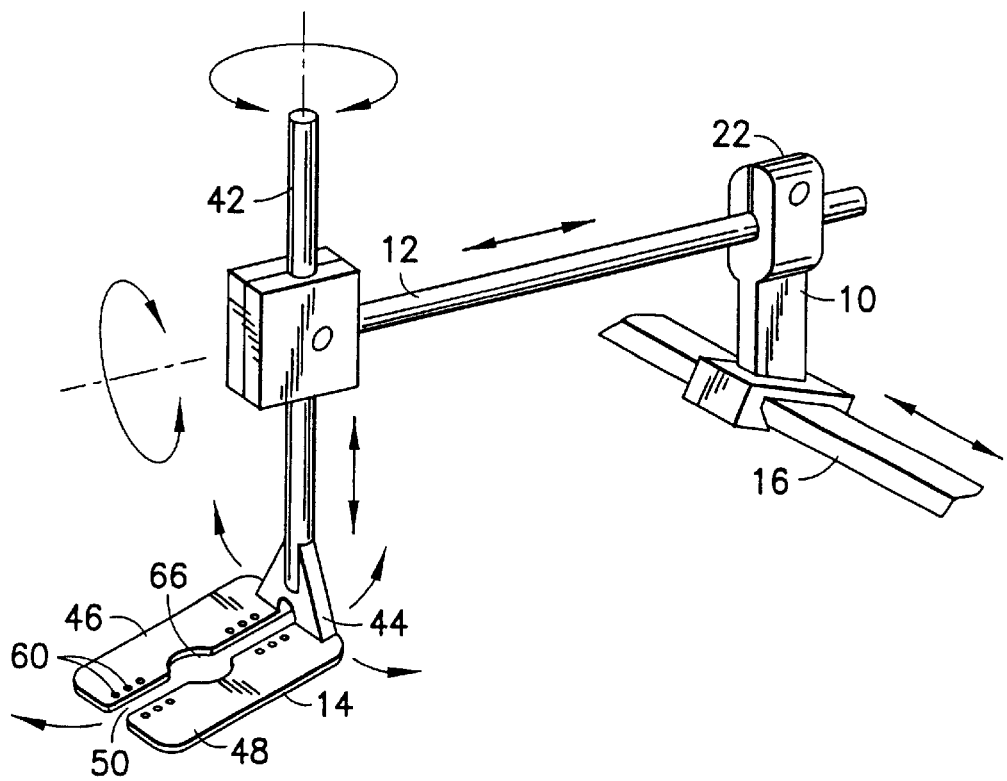
FIG. 6). The joint 22 may be fixed in position as a result of tightening a wing nut 24.

The degrees of freedom of upright 10 and crossbar 12 or 32 allow this joint 26 to be positioned as required on a fixed plane above the operating area and to be aligned at any optional solid angle (cf. FIG. 6). Furthermore, this joint 26 is designed such that it can accommodate a shaft 42 of the platform 14 and secure this in position in seconds as a result of tightening the wing nut 28.

Figure 9:
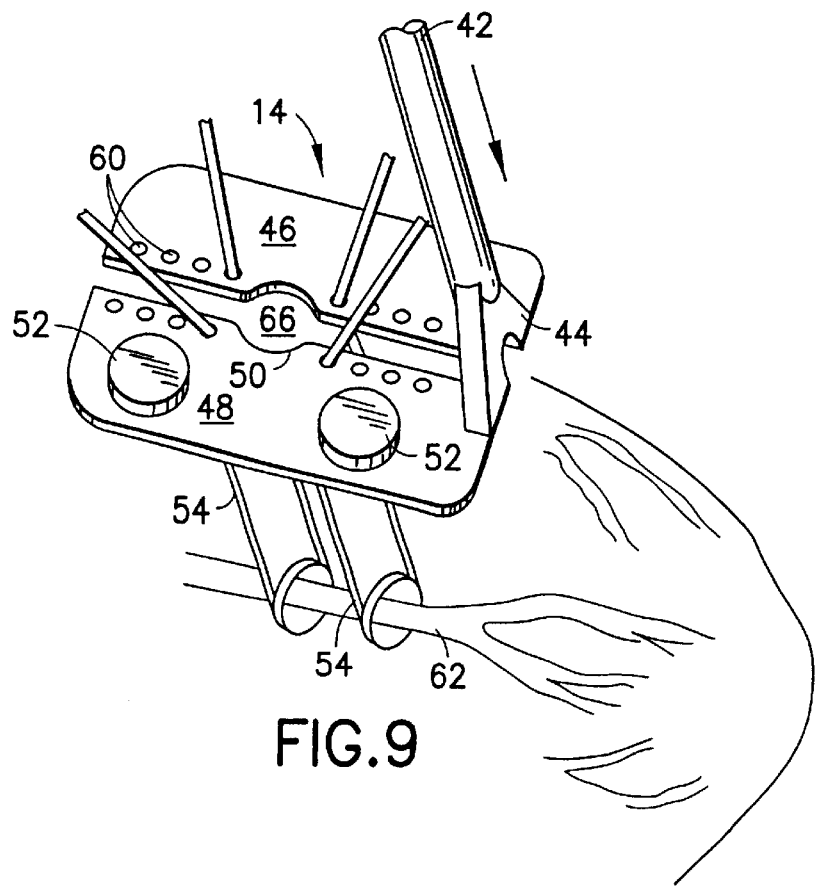
Figure 10:
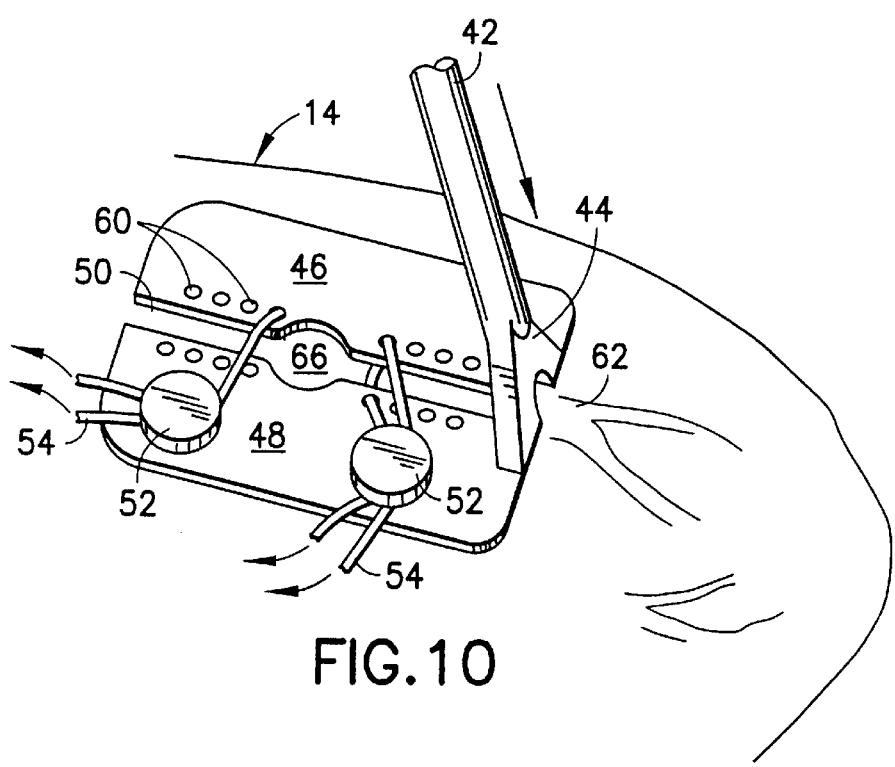
Figure 11:
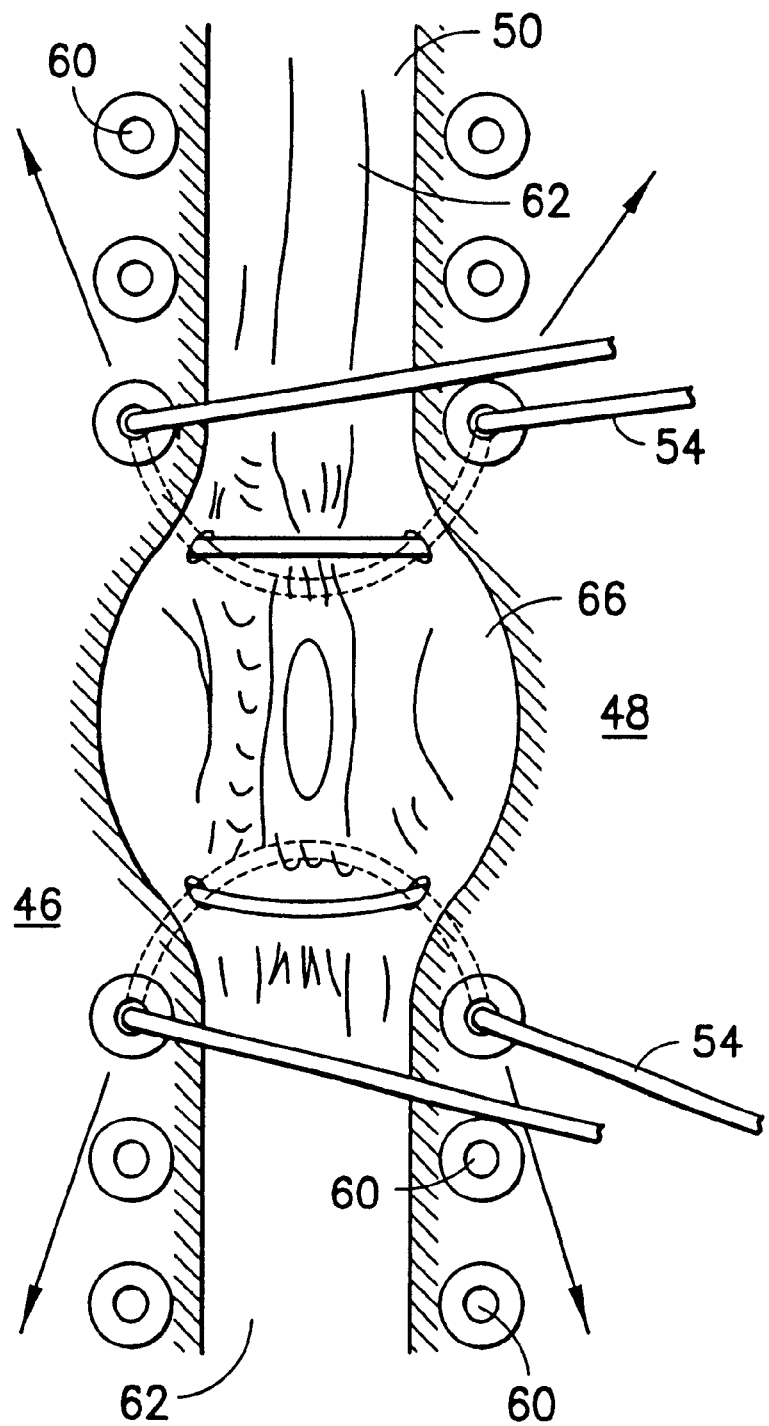

The platform 14 comprises the above-mentioned shaft 42, which bears at its lower end a bridge 44, the bases of which again bear two platform blades 46 and 48. The platform 14 forms between its fork blades 46 and 48 an intermediate space 50 which serves to accommodate a coronary vessel, as illustrated in FIGS. 9 to 11. The intermediate space has, for example, a width of 6.5 mm. Furthermore, fixing means 52 are formed on at least one fork blade 48 and these serve to receive and secure winding means 54 (cf. FIG. 10).

Figure 1:
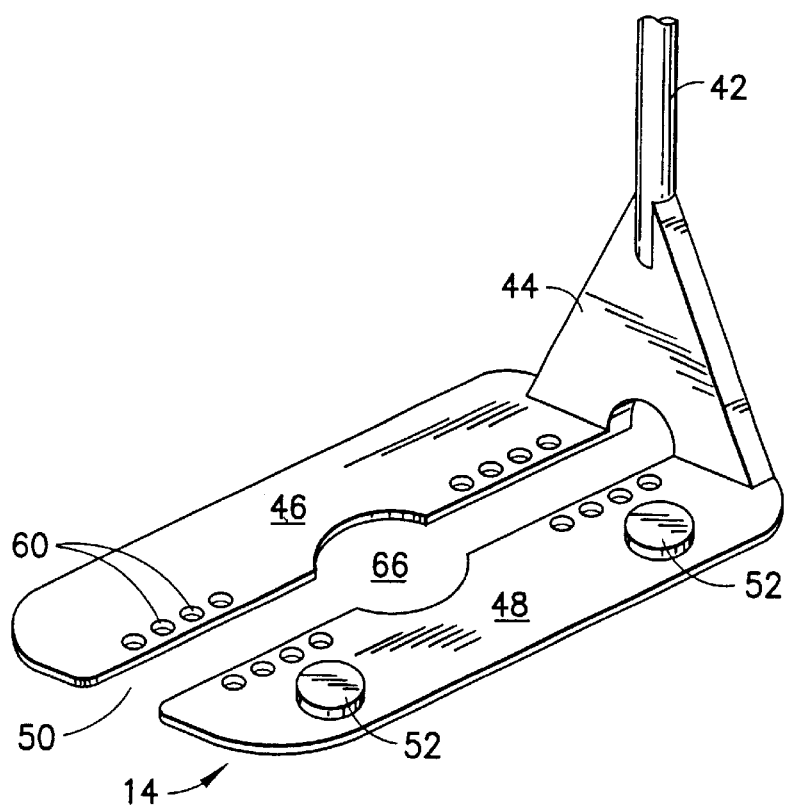
Figure 2:
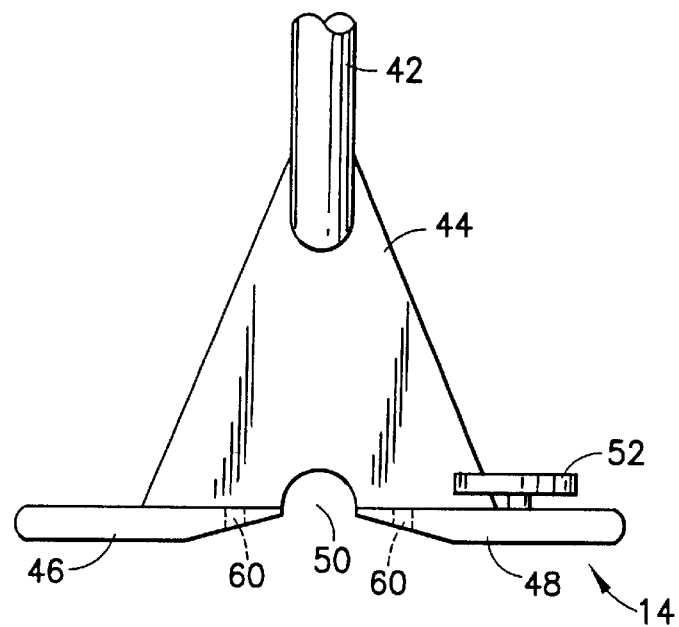
Figure 3:
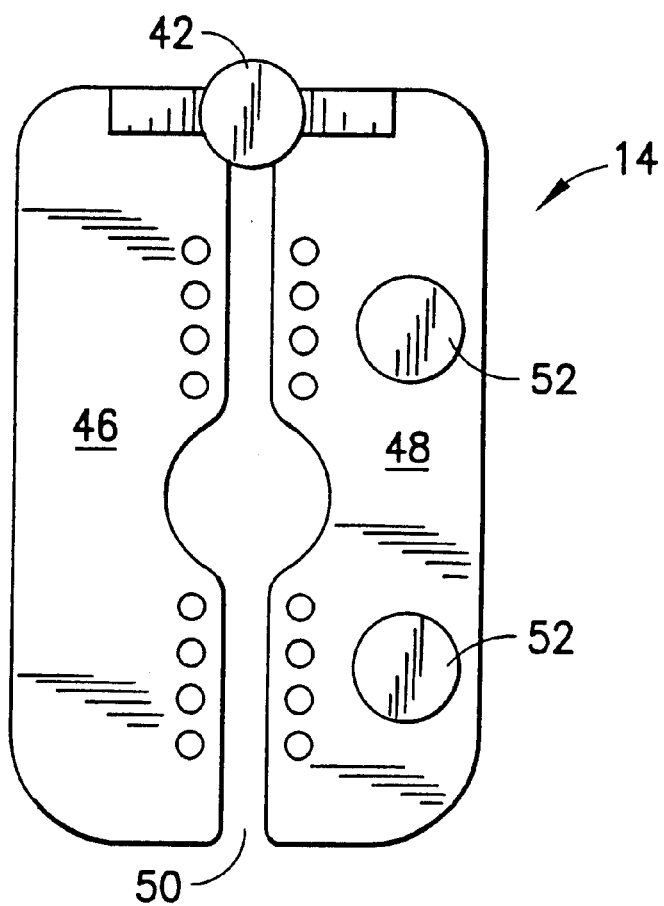
Figure 4:
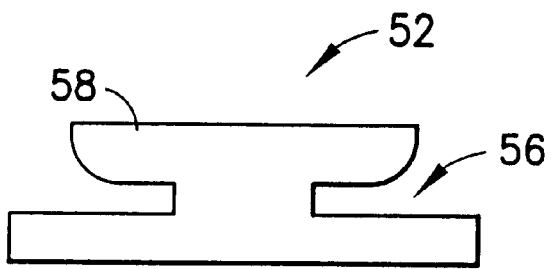
Figure 8:
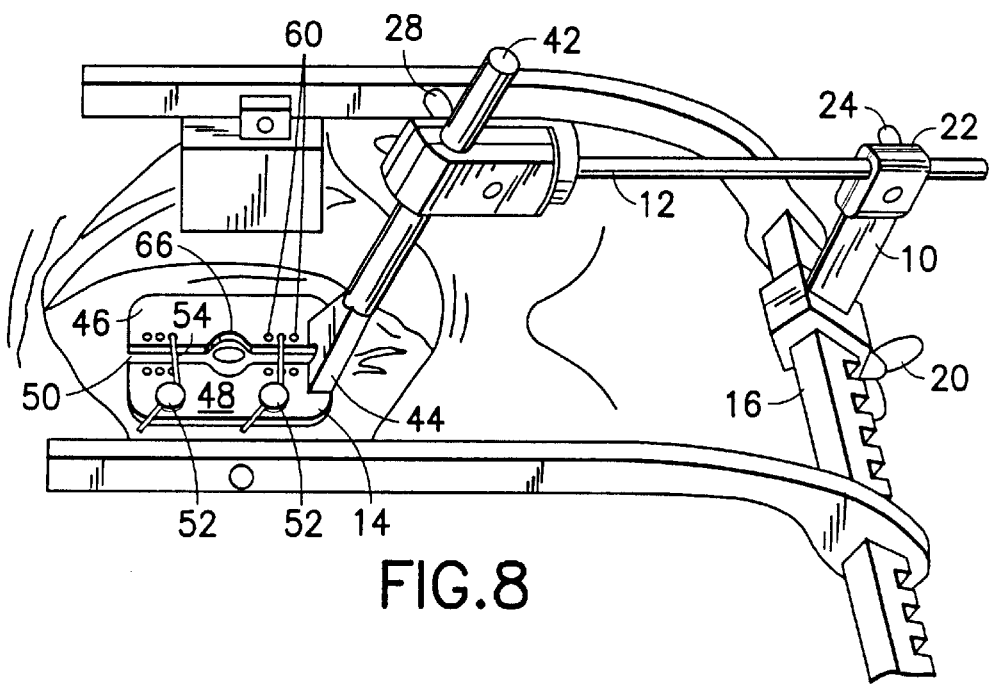

The fixing means are designed, for example, like mushrooms, as illustrated in FIG. 4, wherein a gap 56 under the mushroom head 58 serves to receive and secure the winding means 54. This is apparent, for example, from FIGS. 8 and 10.

Furthermore, openings 60, through which the winding means 54 can be guided, are formed on the fork or platform blades 46 and 48, as illustrated in FIGS. 9 to 11. The openings 60 serve as bearing points for the means 54 which are, for example, vessel loops 54 and so the looped coronary vessel 62, as is apparent from FIGS. 9 to 11, can be clamped and fixed in the gap or intermediate space 50. For a good accessibility of the coronary vessel 62 in the intermediate space 50, the latter has, in addition, a circle-like enlargement 66 (cf., in particular, FIG. 11).

Figure 13:
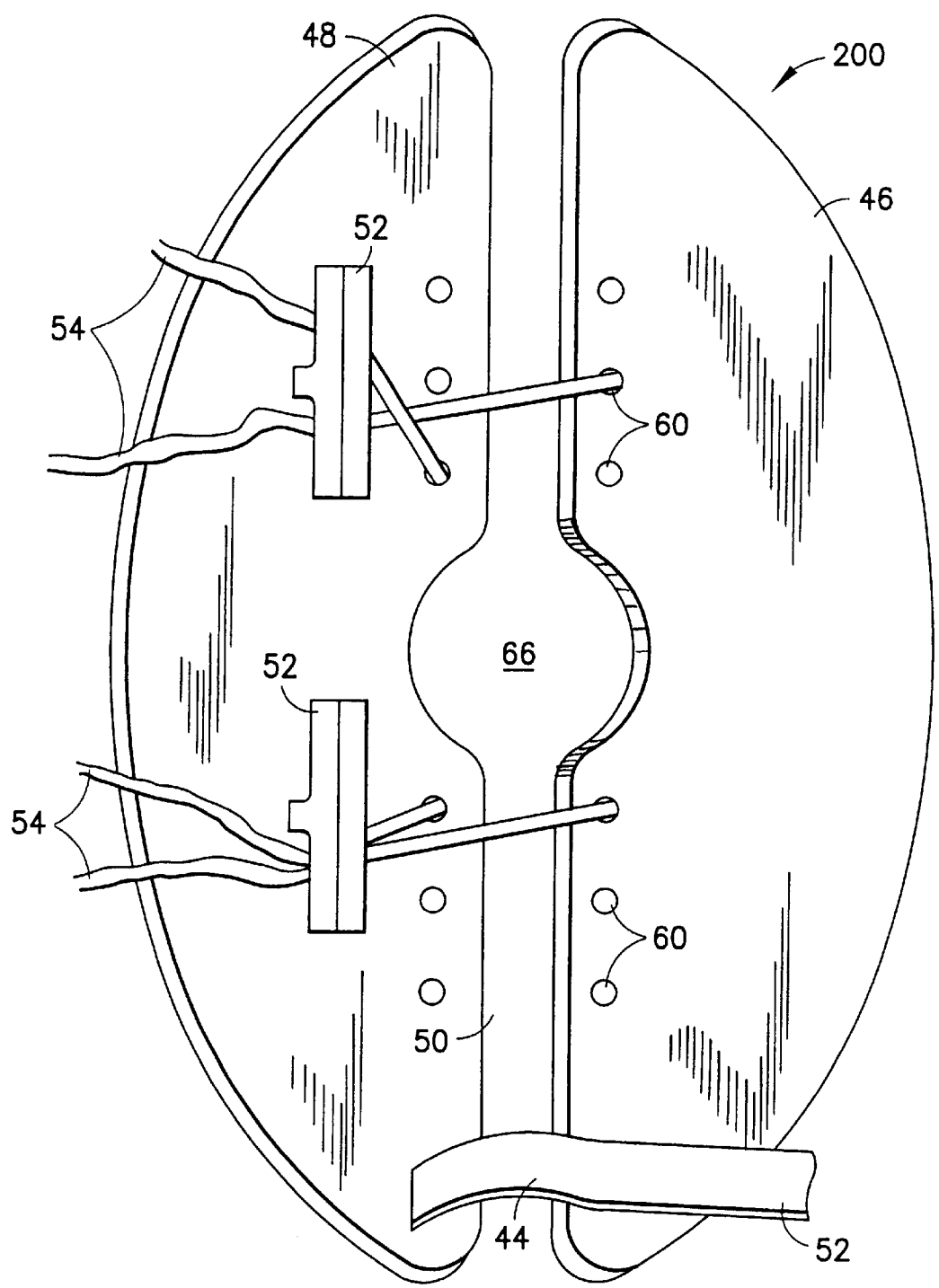

FIG. 13 shows a second advantageous design 200 of the platform, wherein the fixing means 52 are in the form of a strip.

Figure 14:
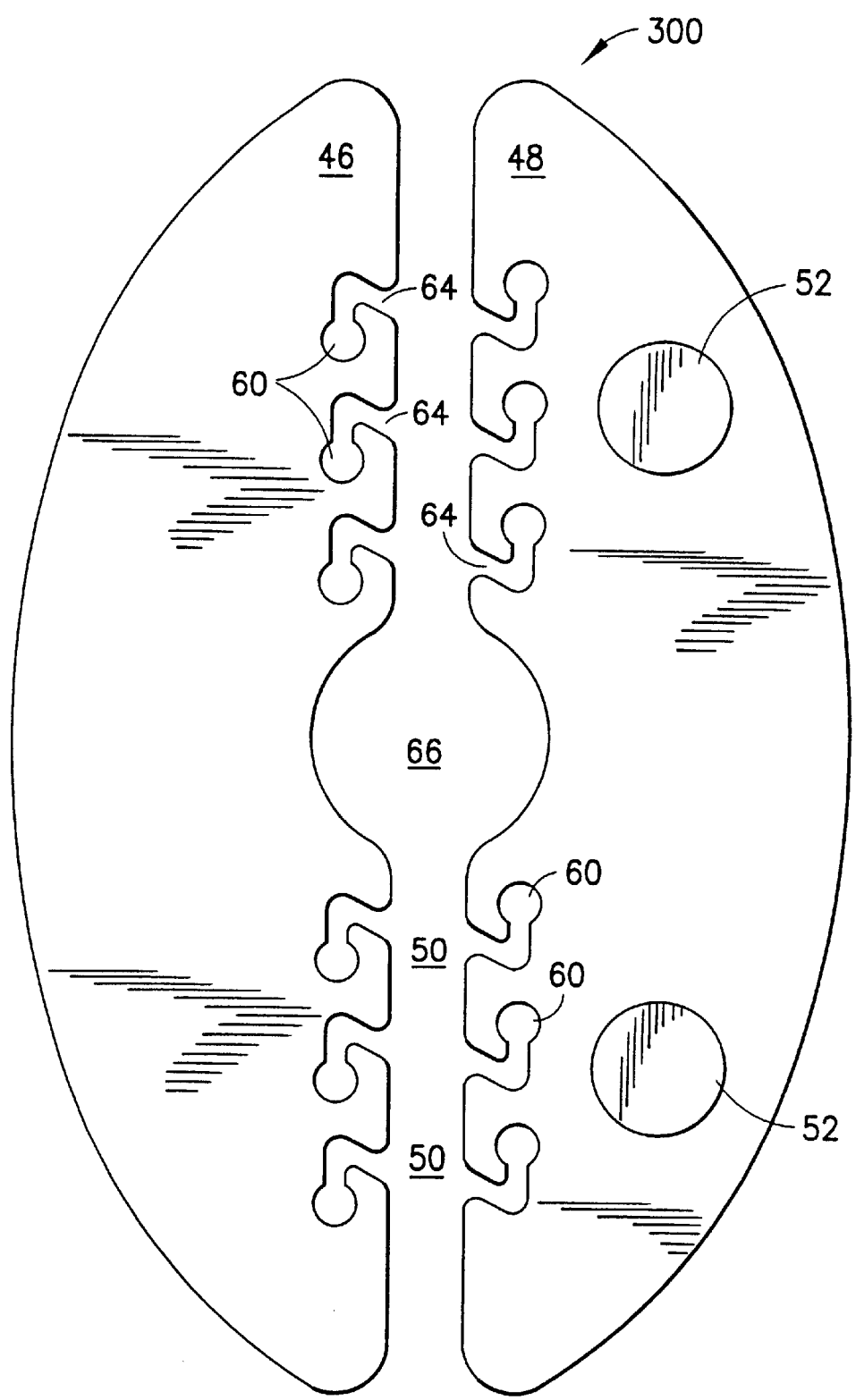

FIG. 14 shows a third preferred embodiment of the platform, wherein the openings 60 are connected to the intermediate space 50, in addition, by slots 64. In this way, an irksome threading of the vessel loops 54 into the openings 60 is dispensed with. The vessel loops 54 are, instead, placed in the corresponding openings 60 via the slots 64. In this respect, the slots 64 are preferably of a hook-like or S-shaped design so that any unintentional slipping of the vessel loops 54 out of the openings 60 is effectively prevented.

Handling, operation and additional details of the inventive device are explained in greater detail in the following with reference to FIGS. 8 to 12.

The device preferably consists of surgical steel and the surface is treated by glass bead jets.

The upright 10 bears the crossbar 12 and represents the transition to the respective retractor 16, 18, for example, a BIRNBAUM retractor. It is preferable to provide interchangeable adapter modules or a universal adapter in order to be able to connect the inventive device to all retractors currently in use.

In an advantageous further development, a ball joint is provided which makes it possible to turn the crossbar 12 into any reasonable solid angle as well as to be able to slide it back and forth in the joint. Such a variation simplifies the adjustment of the platform.

The construction of the crossbar joint 26 takes into consideration in its dimensions the requirements of high stability, free view, rapid accommodation and locking as well as just as quick a release of the platform shaft 42.

The pressure spring 36 contained in the joint 26 is preferably surrounded completely by a sleeve in order, in the case of any breakage of the spring, to make the uncontrolled dropping of broken pieces into the breast cavity impossible.

In order to make the frictional resistance of the heart as slight as possible, the underside of the platform blades 46 and 48 is preferably polished.

The gap 50 with its round enlargement 66 holds the LAD 62 with its blunt edges. The holes 60 for the vessel loops 54 are positioned in four arrangements of four to the right and left of the round enlargement 66 along the edges of the gap. Of great importance for safety is the complete desharpening and polishing of these holes 66 so that any separation of the vessel loops 54 is avoided in any case.

Two studs 52 serve to lock the vessel loops 54. For this purpose, the vessel loops 54 in the form of hollow tubes or hollow rubber bridles are wound around the base of the studs 52 and are already securely fixed after one turn.

During operations, the device is presented without platform 14 once the LAD 62 has been wound around with vessel loops 54 in front of and behind the anastomosis area. The crossbar 12 is located in a central position based on experience, the upright joint 22 is closed, the crossbar joint 26 is open and aligned parallel to the upright 10. The wing nuts 20, 24, 28 point to the assistant.

The device is placed on the base of the BIRNBAUM retractor 16 and secured in a central position based on experience by tightening the wing nut 20 at the base of the upright 10.

As a result of alternating releasing and closing of the joints 22, 26, the device is aligned such that the sleeve of the crossbar joint 26 points vertically onto the anastomosis area, offset through approximately three cm to the right.

The platform 14 is now brought up and the vessel loops 54 threaded in (FIG. 9).

The platform shaft 42 is then inserted into the opened crossbar joint 26 and the joint 26 closed but not yet secured.

This is followed by the sensitive restraining, centering and lowering of the platform 14 with constant assessment of the factors minimum traumatism of the LAD 62 by the vessel loops 54'', minimum hindering of cardiac action, "optimum alignment of the platform 14 (tangentially to the surface of the heart, anastomosis area centered, platform gap 50 parallel to the LAD 62) and, finally, optimum immobilization of the anastomosis area.

As illustrated in FIG. 10, the vessel loops 54 are subsequently secured to the studs 52. The surgeon can now begin with the procedure, wherein he has in front of him a coronary vessel 62 which is immobilized in an optimum manner and aligned in a fixed manner.

Figure 12A:
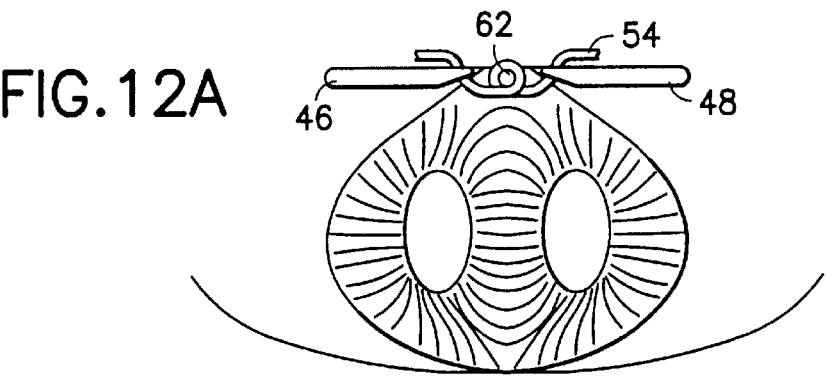
Figure 12B:
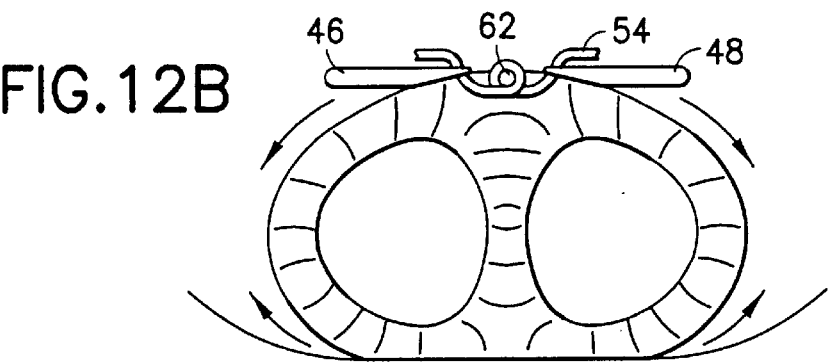
Figure 12C:
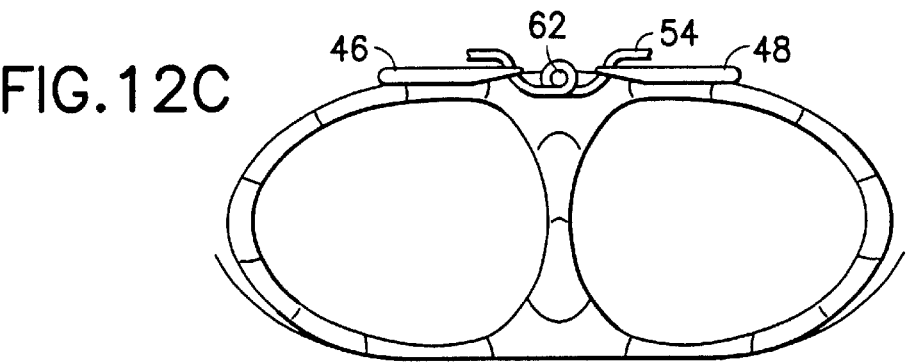
Figure 12D:
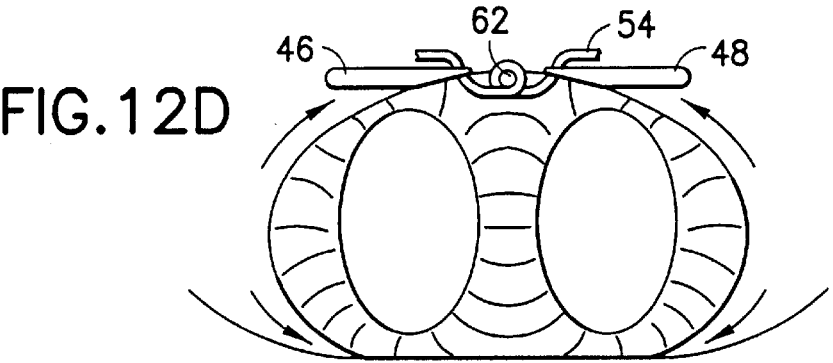

FIGS. 12A to 12D illustrate the situation with a fixed coronary vessel 62 at the beating heart in the contracted state (FIG. 12A), in the expansion phase (FIG. 12B), in the expanded state (FIG. 12C) and in the contraction phase (FIG. 12D). This shows clearly that despite a heart beating in an unhindered manner the coronary vessel 62 is practically immobilized completely.

FIG. 9 shows in detail the attachment of the inventive device on the heart. The LAD 62 is wound around with vessel loops 54 to the right and left adjacent the anastomosis area and these are threaded into suitable holes or openings 60 of the platform 14, 46, 48. The platform is then lowered, wherein the vessel loops 54 are held slightly under tension.

When the platform 14, 46, 48 is in position (cf. FIG. 10), the vessel loops 54 are subjected to tension in such a manner that the LAD 62 is closed and the anastomosis area is centered in the enlargement 66 of the platform gap 50.

Figure 15:
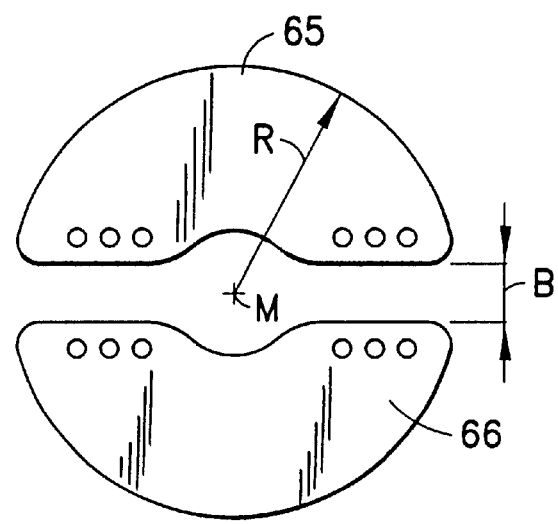
Figure 16:
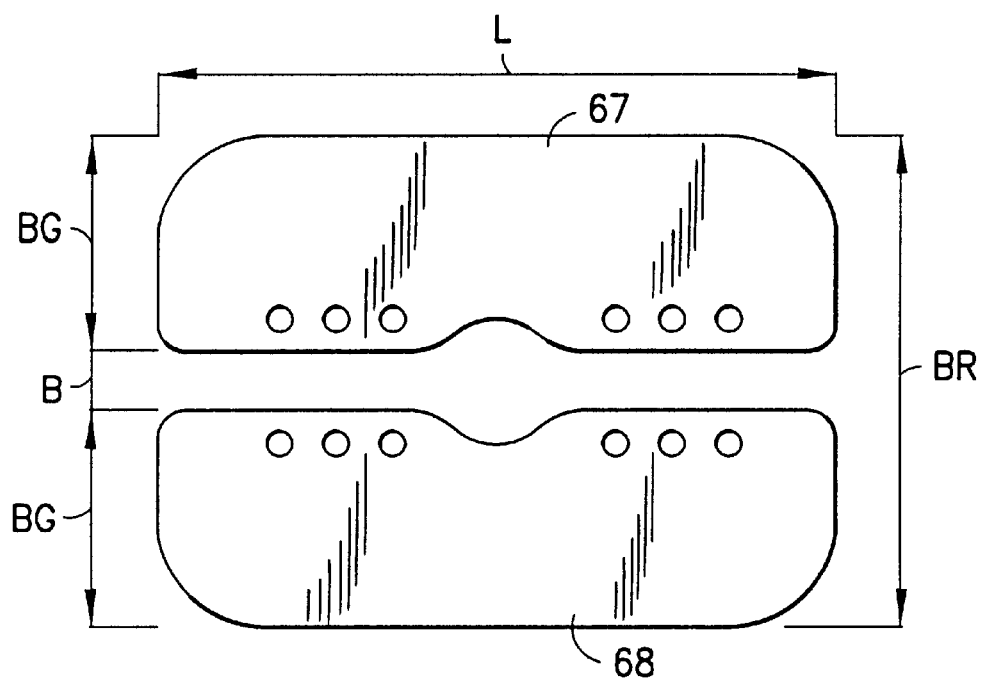

FIGS. 15 and 16 show schematically two embodiments of the fork surfaces as contact surfaces. With the embodiment according to FIG. 15, the two fork surfaces 65, 66 supplement one another together with the intermediate space 50 to form a circular surface with an external radius R, wherein the width B of the intermediate space 50 corresponds approximately to one third of the radius R. The contact surface area thus formed is preferably 7 cm$^2$.

With the embodiment according to FIG. 16, the two fork surfaces 67, 68 form with the intermediate space 50 approximately a rectangle with the length L and a width B which corresponds to the sum of the widths BG of the fork surfaces 67, 68 and the width B of the intermediate space 50. The contact surface area thus formed is preferably 30 cm$^2$.

What is claimed is:

1. A device adapted to locally immobilize a beating heart, comprising:
    a fork shaped platform with first and second fork blades extending essentially parallel and forming an intermediate space therebetween;
    said intermediate space having a width adapted to accommodate a coronary vessel, said width being in a range of about one to five times a width of the coronary vessel to be accommodated;
    a first opening adjacent to said intermediate space on said first fork blade;
    a second opening adjacent to said intermediate space on one of said first and second fork blades; and
    means, adapted to be guided through said openings and secured to a stud provided on at least one of said fork blades, for winding around the coronary vessel;
    said stud having head and post portions that together form a mushroom-shaped cross section, thereby providing a gap for the winding means between the respective fork blade and head portion.

2. A device as defined in claim 1 wherein at least one curved enlargement is provided in said intermediate space.

3. A device as defined in claim 2 wherein said curved enlargement has a diameter in the range of about 8 mm to 12 mm.

4. A device as defined in claim 3 wherein said diameter is 10 mm.

5. A device as defined in claim 1 wherein said second opening is formed on said first fork blade.

6. A device as defined in claim 1 wherein said first and second openings are bores.

7. A device as defined in claim 1 wherein slots are provided which extend from the intermediate space to the openings in the associated fork blade(s).

8. A device as defined in claim 7 wherein said slots are in the form of a hook or S shape.

9. A device as defined in claim 1 wherein at least one of said first and second fork blades is chamfered towards the intermediate space on a side adapted to abut the heart.

10. A device as defined in claim 1 wherein at least one of said first and second fork blades is chamfered towards the intermediate space on a side adapted to abut the heart, at a chamfer angle in a range of about 5 to 15 degrees.

11. A device as defined in claim 10 wherein said chamfer angle is 10 degrees.

12. A device as defined in claim 1 wherein said intermediate space has a width in a range of about 4 mm to 10 mm.

13. A device as defined in claim 12 wherein the width of said intermediate space is 6.5 mm.

14. A device as defined in claim 1 wherein said means for winding around the coronary vessel comprises at least one of a thread or a vessel loop.

15. A device as defined in claim 1 wherein the width of said intermediate space is in a range of about one to two times the width of the coronary vessel to be accommodated by the intermediate space.

16. A device as defined in claim 1 wherein the width of said intermediate space is in a range of about one to three times the width of the coronary vessel to be accommodated by the intermediate space.

17. A device as defined in claim 1 wherein the width of said intermediate space is in a range of about two to three times the width of the coronary vessel to be accommodated by the intermediate space.

18. A device as defined in claim 1 wherein the width of said intermediate space is established such that the coronary vessel can be accommodated with a lateral distance from the vessel to the fork blades of no greater than the width of the coronary vessel.

19. A device as defined in claim 1 wherein the fork blades are connected to one another via a bridge having an essentially semicircular recess between two arms, each arm having one of the fork blades extending from an end thereof.

20. A device as defined in claim 19 wherein the semicircular recess has a radius in a range of about 2 mm to 5 mm.

21. A device as defined in claim 20 wherein said radius is 3.25 mm.

22. A device as defined in claim 1 wherein:

surface areas of said fork blades and said intermediate space cooperate to form an approximately circular ring; and said ring has a radius from its outer circumference to a fictitious center thereof which is about three times the width of said intermediate space.

23. A device as defined in claim 22 wherein the fork blades have a contact surface area of about 7 cm$^2$.

24. A device as defined in claim 1 wherein:

surface areas of said fork blades and said intermediate space cooperate to approximate a rectangle; and the length of the surface area of one fork blade corresponds approximately to twelve times the width of said intermediate space.

25. A device as defined in claim 24 wherein the fork blades have a contact surface area of about 30 cm$^2$.

26. A device as defined in claim 1 wherein:

surface areas of said fork blades and said intermediate space cooperate to approximate a rectangle; and the width of the surface area of one fork blade corresponds approximately to five times the width of said intermediate space.

27. A device as defined in claim 26 wherein the fork blades have a contact surface area of about 30 cm$^2$.

* * * * *